United States Patent [19]

Yamashita

[11] 4,363,782
[45] Dec. 14, 1982

[54] DISCRETE TYPE AUTOMATED CHEMICAL ANALYTIC APPARATUS

[75] Inventor: Kiyoshi Yamashita, Otawara, Japan

[73] Assignee: Tokyo Shibaura Denki Kabushiki Kaisha, Japan

[21] Appl. No.: 250,211

[22] Filed: Apr. 2, 1981

[30] Foreign Application Priority Data

Apr. 8, 1980 [JP] Japan .................................. 55-46353

[51] Int. Cl.³ ..................... G01N 35/04; G01N 35/06; G01N 33/48
[52] U.S. Cl. .................................... 422/65; 141/130; 364/497; 422/67; 422/66; 422/102
[58] Field of Search ....................... 422/64, 61, 63, 65, 422/67, 66, 100, 102; 141/130; 364/497, 498

[56] References Cited

U.S. PATENT DOCUMENTS

| | | | |
|---|---|---|---|
| 3,481,709 | 12/1969 | Slone | 422/66 |
| 3,551,112 | 12/1970 | Sequeira et al. | 422/65 |
| 3,576,605 | 4/1971 | Drake et al. | 422/65 X |
| 3,687,632 | 8/1972 | Natelson | 422/65 X |
| 3,723,066 | 3/1973 | Moran | 422/66 X |
| 4,058,367 | 11/1977 | Gilford | 422/67 X |
| 4,260,581 | 4/1981 | Sakurada | 422/65 |
| 4,299,796 | 11/1981 | Hogen Esch | 422/65 X |

*Primary Examiner*—Michael S. Marcus
*Attorney, Agent, or Firm*—Finnegan, Henderson, Farabow, Garrett & Dunner

[57] ABSTRACT

A discrete type automated chemical analytic apparatus wherein two reagent nozzles and specimen nozzle supported by the corresponding carrier members in a vertically movable state are so arranged that said nozzles can be intermittently carried lengthwise of the reaction line formed on the endless conveyor belt and also crosswise of said reaction line; and a sample cassette holding a large number of specimens is made movable lengthwise of the conveyor belt independently of the specimen nozzle.

8 Claims, 6 Drawing Figures

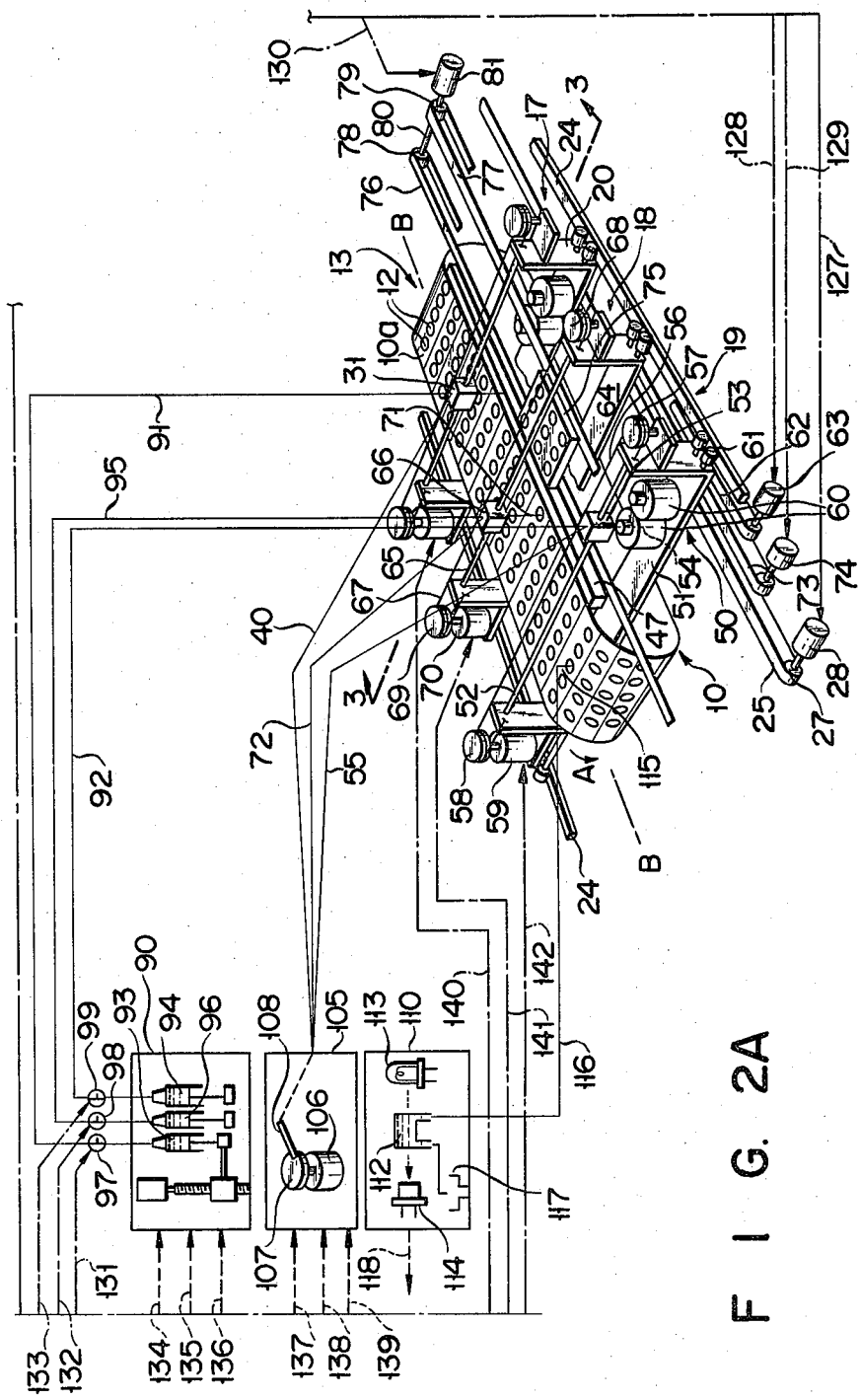
F I G. 2A

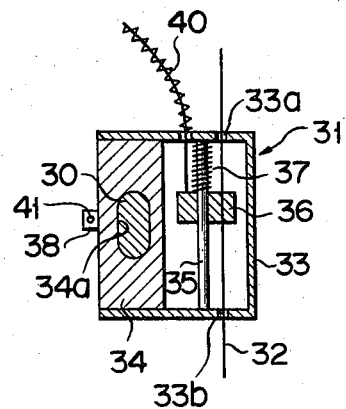
F I G. 4
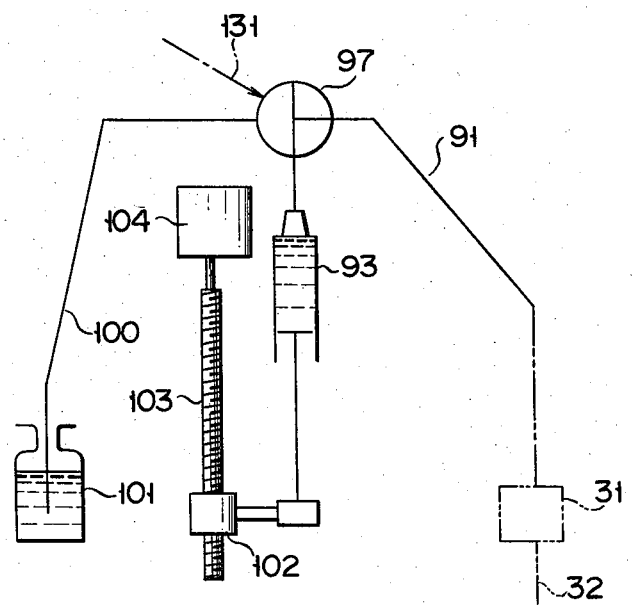
F I G. 5

DISCRETE TYPE AUTOMATED CHEMICAL ANALYTIC APPARATUS

This invention relates to an automated analytic apparatus, and more particularly to the so-called discrete type automated chemical analytic apparatus which is capable of continuously analyzing a large number of specimens with respect to a plurality of items of examination in a single reaction channel.

Recently, it has assumed greater importance to carry out the analytic procedure of a specimen for diagnosis of a disease and provide required data. Moreover, the number of specimens and their items of examination are progressively increasing. In view of such circumstances, therefore, automation of an analytic procedure has become a problem of urgency in hospitals, laboratories or centers which undertake medical examination work. What is most demanded in this case is an improved automated chemical analytic apparatus which enables a limited personnel and space to furnish analytic diagnostic data closely related to human life without errors.

In this connection, the following points should be taken into consideration:

(1) Analysis of an extremely minute amount of a specimen and reagent should be carried out at low cost.

(2) A large number of specimens should be quickly analyzed and the resultant data should be immediately obtained.

(3) A limited personnel should be enabled to carry out analytic procedures of a larger number of specimens with respect to numerous items of examination.

(4) Accurate and precise data should be furnished in good time.

(5) The subject analytic apparatus should be made sufficiently compact to be installed in a limited space.

With the conventional automated analytic apparatus, noticeable improvements have been made in respect of the above-listed requirements. Particularly with the first and second items, noteworthy improvements have been accomplished. With the other items, however, improvements attempted to-date can not be regarded as fully satisfactory.

The known discrete type automated chemical analytic apparatus in general use is of the so-called fixed type, wherein the points at which a specimen and reagent are pipetted are fixed, in other words, a distance between a pipetting pump and pipetting point is always defined in accordance with an item of examination. Some semifixed type analytic apparatuses have also been proposed wherein the pipetting point can be slightly shifted, if necessary. Generally speaking, the pipetting point can not be freely varied in a conventional apparatus. In other words, the prior art analytic apparatus is not of the type which enables a given amount of a reagent or specimen to be pipetted at any desired point along a reaction line. Therefore, limitation is imposed on the conventional analytic apparatus in respect of the latitude of application, that is, in the sense that a reaction time should be properly chosen in accordance with individual reagents and specimens. Inevitably, therefore, occasions arise in which an improper reaction has to be undertaken, resulting in a decline in the reliability of obtained data of examination.

Consequently, the examiner has hitherto manually changed a pipetting point or an amount of a liquid to be pipetted in order to obtain more accurate data. Demand has therefore been made to automate these manual procedures.

For reference, the aforementioned analytic apparatus is disclosed in the U.S. Pat. No. 3,432,271. In this connection, the Japanese patent disclosure 54-5790 may be cited which has attempted to automate the pipetting of a reagent in order to simplify the control of an automated chemical analytic apparatus. Brief description is now given with reference to FIG. 1 of the arrangement of the chemical analytic apparatus of said Japanese Pat. No. 54-5790. This disclosed analytic apparatus comprises:

(a) a serum pipetting mechanism periodically repeating the same action regardless of specimen data;

(b) a nozzle through which a serum sample is supplied as a specimen from the mechanism (a);

(c) a washing tank used to clean the outer wall of the nozzle (b);

(d) a main computer for sending forth an instruction based on specimen data;

(e) a large number of first reagent containers;

(f) a turntable on which the first reagent containers (e) are carried and which is driven upon receipt of an instruction from the main computer (d);

(g) a pipette mechanism for dripping the first reagent;

(h) a nozzle connected to said pipette mechanism (g);

(i) a washing tank used to clean the outer wall of the nozzle (h);

(j) a large number of second reagent containers;

(k) a turntable on which the second reagent containers (j) are carried and which is driven upon receipt of an instruction from the main computer (d);

(l) a pipette mechanism for dripping the second reagent;

(m) a nozzle connected to the pipette mechanism (l); and (n) a washing tank used to clean the outer wall of the nozzle (m).

Description is now given of the operation of an automated chemical analytic apparatus (FIG. 1) set forth in the Japanese Pat. No. 54-5790. This chemical analytic apparatus further comprises a specimen feeder (q) carrying a plurality of linearly arranged specimen container (p) each holding, for example, serum. Where one of the specimen containers (p) is brought to a point at which a serum is sucked out of the container (p), then the specimen feeder (q) temporarily ceases to be moved. During the rest of the specimen feeder (q), the aforesaid pipette mechanisms (a, g, l) carry out a prescribed action on a reaction line (s) along which a large number of reaction tubes (r) are set side by side. The serum sucked out of the serum container (p) by the pipette mechanism (a) is diluted with deionized water. The diluted serum is pipetted from the specimen container (p) into the corresponding one of the reaction tubes (r) linearly arranged on the reaction line (s) through the nozzle (b). Where one of the reaction tubes (r) is made to face the nozzle (h) for the first reagent while traveling to the right as viewed in FIG. 1, then the turntable (f) for the first reagent is rotated in the direction of an indicated arrow to an extent corresponding to the previously supplied specimen data. When the rotation is brought to rest, the first reagent held in the reagent container (e) set at a prescribed pipetting point is dripped into the reaction tube (r) by the pipette mechanism (g). Where the reaction tube (r) further travels to the second reagent nozzle (m), then the second reagent is drawn into the reaction tube (r) by the pipette mechanism (l).

The serum solution which was subjected to the above-mentioned reaction procedure has its composition is determined by a spectroscope (t) disposed at the terminal end of the reaction line. The result of the spectroscopic determination is transmitted to the main computer (d) through an interface device (u), and also is visibly printed out at an operation and control section (v).

Application of a turntable in the above-described chemical analytic apparatus of the Japanese Pat. No. 54-5790 enables a proper reagent to be automatically selected, eliminating the troublesome work of manually exchanging reagent containers. Further, the analytic apparatus automates the suction and pipetting of a serum and reagent, and enables the uniform operation of a control system and the simplification of its arrangement, thereby assuring a high reliability.

With the aforementioned analytic apparatus, however, the points at which the suction and pipetting of a serum and reagent are carried out are all fixed in place. With the apparatus, therefore, it is impossible to control an interval between the point of time at which pipetting is carried out and that at which a final analysis is performed. For instance, even where a specimen requiring an instant analysis is presented and a reagent reaction relative to the specimen can be finished in a short time, the quick operation of the analytic apparatus of the above-mentioned disclosed patent application is obstructed by the rather lengthy reaction time prescribed in the specification, presenting difficulties in meeting urgent requirements. In other words, the apparatus lacks the freedom to match a reaction time with a specimen to be examined. This means that not only time loss but also an excessively protracted reaction between a serum and reagent results, leading to the production of inaccurate data. Moreover, with the analytic apparatus, turntables occupy a considerably large space, presenting difficulties in rendering the apparatus compact.

It is accordingly the object of this invention to provide a novel compact discrete type automated chemical analytic apparatus which is freed of the above-mentioned difficulties accompanying the conventional automated chemical analytic apparatus, enables a reaction time to be adjusted freely and properly in accordance with the type of specimen and the items of examination, is increased in the lattitude of application, and assures the accurate and speedy examination of a large number of specimens.

To attain the above-mentioned object, this invention provides a discrete type automated chemical analytic apparatus, wherein a specimen discharge nozzle is supported on a carrier member in a vertically movable state; the carrier member can be moved to any desired extent in the direction in which a conveyor carrying linearly arranged reaction tubes is driven that is, the direction in which a reaction line extends, and also crosswise of the reaction line, namely, at right angles to the direction in which the conveyor is driven, the carrier member being rendered freely movable everywhere along a two-dimensional plane; a mechanism for effecting the crosswise movement of the specimen carrier member is supported on a mechanism for carrying out the longitudinal movement of the specimen carrier member, both mechanisms jointly constituting a movable unit; the arrangement of the movable unit is also adopted for a reagent carrier member for supporting a reagent discharge nozzle; the reagent carrier member is rendered freely movable to any extent lengthwise and crosswise of the reaction line along a two-dimensional plane; reagent containers are mounted on a movable frame unit for reagents to be longitudinally moved with the reagent carrier member; a rectangular specimen cassette supporting specimens arranged substantially in the matrix form is disposed by the side of a conveyor, is rendered movable to any extent in parallel with the reaction line, and is fitted with a conveyor belt extending in parallel with the reaction line.

A discrete type automated analytic apparatus according to a preferred embodiment of this invention has the following advantages that a position in which a specimen is pipetted and/or a position in which a reagent is pipetted can be freely determined, enabling an optimum and minimum reaction time to be always selected, thereby eliminating the so-called waiting time, and consequently the subject apparatus is rendered immediately applicable to the urgent examination of a specimen; where necessary, a reaction time can be conversely prolonged; the apparatus has a large lattitude of application by meeting the requirements to examine a large number of specimens and analyzing many items of examination; and it is possible to establish optimum conditions for the examination of a specimen and assure a high precision of analysis.

The analytic apparatus of the invention eliminates the necessity for the examiner to manually define a pipetting position each time, and enables a specimen or reagent nozzle to be set in an automatically determined position by means of a program. In other words, the present analytic apparatus makes it unnecessary to provide many nozzles corresponding to a large number of reaction tubes mounted on the reaction line, thereby assuring the simplification of a conduit arrangement and the noticeable elevation of the examiner's work efficiency.

The analytic apparatus of the invention is particularly adapted to be used as the so-called multichannel type in which many rows of reaction tubes are mounted in parallel on a conveyor belt. The reason for this is that the specimen and reagent containers can be moved automatically and quickly lengthwise and crosswise of the reaction line to allow for speedy pipetting.

For reference, description is given of an already proposed discrete type multichannel analytic apparatus which has a different arrangement from that of the present invention. This previously proposed multichannel analytic apparatus comprises a plurality of specimen and reagent nozzles for each reaction channel, which are made movable only lengthwise of the reaction line. Thus, the more the channels, the more the reaction tubes and nozzles. Consequently said proposed multichannel analytic apparatus has the drawback that the arrangement is unavoidably rendered complicated. In contrast, the multichannel analytic apparatus of the invention elimates the necessity of increasing a number of specimen and reagent carrier members, even where the rows of reaction channels increase in number, and consequently can be simplified in arrangement and rendered compact.

Further with the analytic apparatus of the invention, reagent and specimen containers are arranged closely along a conveyor belt, thereby allowing specimen and reagent nozzles to be carried from the original positions to the pipetting positions through an appreciably shortened distance, and consequently assuring a speedy pipetting procedure.

This invention can be more fully understood from the following detailed description when taken in conjunction with the accompanying drawings, in which:

FIG. 1 schematically shows the arrangement of a prior art automated analytic apparatus;

FIG. 2A is a schematic oblique view of a discrete type automated chemical analytic apparatus embodying this invention;

FIG. 4 is an enlarged cross-sectional view of a carrier member as taken on line 4—4 of FIG. 3; and FIG. 5 is a schematic enlarged view of the pumping mechanism of FIG. 2A for detailed description.

Description is now given with reference FIGS. 2A to 5 of a discrete type automated chemical analytic apparatus embodying this invention.

Referring to FIG. 2A, a wide endless conveyor belt 10 is intermittently driven in a direction indicated by an arrow A by a drive shaft (not shown), a large number of reaction tubes 12 are mounted on the belt 10 lengthwise arranged in the matrix form of 5 rows or 5 channels. A group of reaction tubes which are linearly set on the top run 10a collectively constitute a reaction line 13. A one dot-dash line B—B denotes a control reaction line or channel 13. A mechanism for supporting the reaction tubes 12 which is already known is not indicated in detail. The right side of the conveyor belt 10 represents its leading end and the left side its terminal end.

Figure 3:
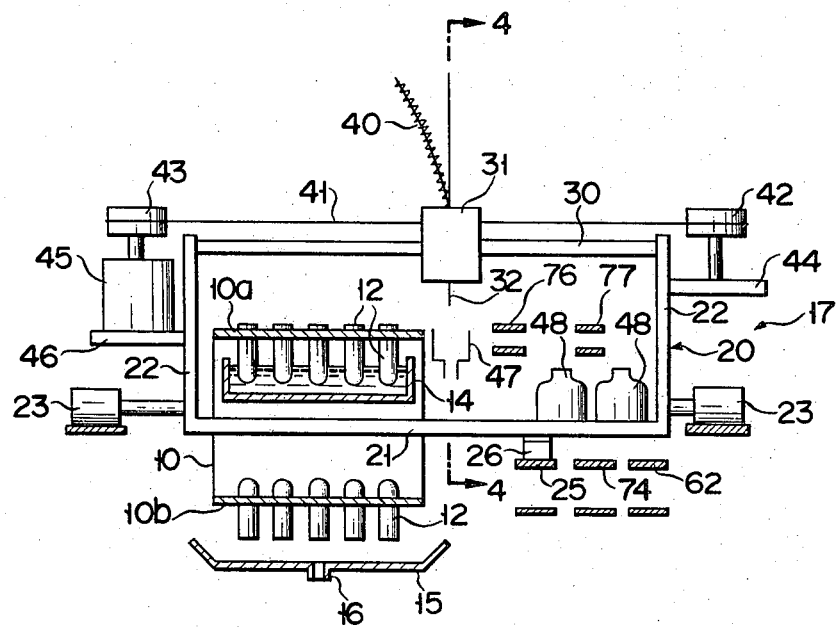
FIG. 3 is an enlarged view as taken on line 3—3 of FIG. 2A.

Referring to FIG. 3, the reaction tubes 12 jointly constituting the reaction line 13 are partly dipped in a thermostat bath 14 for acceleration of reaction between a specimen and reagent in said tubes. A waste receptacle 15 is provided below the bottom run 10b of the conveyor belt 10 to collect the excess portions of the reacted specimen and reagent which have been drawn off the reaction tube 12.

Three movable units 17, 18, 19 (FIG. 2A) are spatially set in a state transversing the conveyor belt 10. The central movable unit 18 is used to pipette a specimen liquid. The movable unit 17 lying on the right side of the central movable unit 18 is used to pipette the a first reagent. The movable unit 19 set on the left side of the central movable unit 18 is applied to pipette a second reagent.

Description is now given with reference to FIG. 3 of the first reagent-pipetting unit 17. This unit 17 comprises a U-shaped frame body 20 formed of a base frame member 21 almost horizontally extending between the top run 10a and bottom run 10b of the conveyor belt 10 and paired vertical frame members 22 extending upward from both ends of the base frame member 21. The lower end portions of the paired upright frame members 22 are each fitted with a pair of rollers 23 (FIG. 2A) rotatable by means of a pivotal shaft. All the pairs of rollers 23 are engaged with the guide bars 24 extending along both sides of the reaction line 13 is rolling relationship. Accordingly, the frame body 20 is supported in a state slidable lengthwise of the reaction line 13. The bottom plane of the base frame member 21 is fixed by means of a fitting attachment 26 (FIG. 3) to a drive belt 25 running in parallel with the reaction line 13. This drive belt 25 (FIG. 2A) is connected to a pulse motor 28 by means of an anchoring pulley 27. The pulse motor 28 intermittently drives the frame body 20 lengthwise of the reaction line 13 by means of the belt 25. Part of the belt 25 and the other anchoring pulley are omitted from FIG. 2A.

Both ends of a horizontally extending guide bar 30 (FIG. 3) are fixed to the upper end portions of the paired arms 22. A carrier member 31 is slidably supported by said guide bar 30. A reagent nozzle 32 is supported by the carrier member 31 in a vertically movable state.

Referring to FIG. 4, the carrier member 31 comprises a casing 33, block 34 fixed to the casing 33 and provided with a penetrating hole 34a allowing for the slidable engagement of the guide bar 30, vertically extending guide rod 35 held in the casing 33, fitting block 36 slidably engaged with the guide rod 35, compression coil spring 37 stretched between the underside of the top plate of the casing 33 and the surface of the fitting block 36, and fitting projection 38 rigidly formed on the outer wall of the block 34.

The vertically extending specimen nozzle 32 rigidly penetrates the fitting block 36. The specimen nozzle 32 passes through the openings 33a, 33b respectively formed in the upper and lower portions of the casing 33. A drive wire 40 connected to the later discribed mechanism 105 for vertically driving the specimen nozzle 32 is fixed at one end to the fitting block 36. Under a normal condition, the wire 40 holds the fitting block 36 and specimen nozzle 32 in a lifted position (FIG. 4) by the energization of a solenoid against the urging force of the compression coil spring 37. Where the solenoid is deenergized, then the specimen nozzle 32 is let to fall by the urging force of the compression coil spring 37.

The guide bar 30 (FIG. 3) has its cross section shaped substantially like an elliptic form. Therefore, engagement between the guide bar 30 and penetrating hole 34a enables the carrier member 31 to be slidably guided by being retained in such a position as is prevented from rotating about the guide bar 30.

A drive endless wire or belt 41 extending in parallel with the guide bar 30 and crosswise of the reaction line 13 is fixed to the fitting projection 38 formed on the block 34. The endless wire 41 is anchored by a pair of right and left pulleys 42, 43. The shaft of the driven pulley 42 is securely held by a support bracket 44 laterally projecting from one of the vertical frame members 22. The drive pulley 43 is connected to a pulse motor 45 by means of a motor shaft. This pulse motor 45 is mounted on a support bracket 46 laterally projecting from the other vertical frame member 22. The drive of the pulse motor 45 causes the carrier member 31 to slide along the guide bar 30 crosswise of the reaction line 13 by means of the pulleys 42, 43 and drive wire 41.

As seen from FIG. 3, a waste receptacle 47 is disposed close by the right side of the top run 10a of the conveyor belt 10. Two first reagent containers 48 are mounted on the base frame member 21 of the frame body 20. A number of reagent containers 48 and the kinds of reagents may be properly selected in accordance with the items of examination and the kind of a specimen. The reagent containers 48, movable unit 17 and reagent nozzle 32 can be moved together lengthwise of the reaction line 13.

The above description of the right side movable unit 17 of the first reagent also applies to that of the left side movable unit 19 of the second reagent, which has substantially the same construction as the right side movable unit 17. Namely, the left side movable unit 19 comprises a substantially U-shaped frame body 50 (FIG. 2A), guide bar 52 fixed to two upright frame members vertically extending from the base frame member 51, a second reagent carrier member 53 slidably engaged with the guide bar 52, reagent nozzle 54 supported by the carrier member 53 in a vertically movable state, solenoid drive wire 55, drive wire or belt 56 fixed to the carrier member 53, a pair of drive and driven pulleys 58, 57 for anchoring the drive wire or belt 56, and drive pulse motor 59 connected to the drive pulley 58.

With the left side movable unit 19, too, two second reagent containers 60 are mounted on the base frame member 51 of the frame body 50. A number of reagent containers 60 and the kinds of reagents may be properly selected in accordance with the items of examination and the kind of a specimen. The reagent containers 60 and reagent nozzle 54 are moved with the left side movable unit 19 lengthwise of the reaction line 13.

The left side movable unit 19 used to pipette the second reagent is guided like the right side movable unit 17 along the paired guide bars 24 extending lengthwise of the reaction line 13 by means of a pair of right and left rollers 61 (FIG. 2A). The frame body 50 is fitted with a drive belt 62 extending in parallel with the drive belt 25. One of the pulleys anchoring the drive belt 62 is connected to a pulse motor 63. This pulse motor 63 causes the left side movable unit 19 to be intermittently moved along the reaction line 13.

The central movable unit 18 used to pipette a specimen has the same construction as the right and left side movable units 17, 19. Namely, the central movable unit 18 comprises a U-shaped frame body 64 guided along a pair of guide bars extending lengthwise of the reaction line 13 by means of paired rollers, a guide bar 65 fixed to the paired upright frame members of the frame body 64 in a state extending crosswise of the reaction line 13, a specimen carrier member 66 slidably guided along said guide bar 65, a drive wire or belt 67 fixed to the carrier member 66 in a state capable of driving the carrier member 66 along the guide bar 65 crosswise of the reaction line 13, a pair of drive and driven pulleys 69, 68 anchoring the drive wire or belt 67, and a pulse motor 70 connected to the drive pulley 69. The pulse motor 70 and paired pulleys 68, 69 are supported by the frame body 64.

A specimen nozzle 71 is supported by the specimen carrier member 66 in a vertically movable state. A wire 72 for energizing a solenoid is connected to the specimen carrier member 66. A drive belt 73 extending lengthwise of the reaction line 13 is fixed to the frame body 64. The drive belt 73 is connected to a pulse motor 74 by means of a pulley.

The carrier members 66, 53 of the central and left side drive units 18, 19 have substantially the same construction as the carrier member 31 of the right side drive unit 17. For simplification of drawing, the drive belts 25, 62, 73 for urging the movable units 17, 18, 19 lengthwise of the reaction line 13 are partly omitted from FIG. 2A.

The guide bar 30 of FIG. 4 extending crosswise of the reaction line 13 may have any other cross sectional form than indicated in FIG. 4, provided the cross section has such a shape as prevents the rotation of the carrier member.

A specimen cassette 75 for holding specimen containers in which a specimen sampled from an examinee is received has a rectangular flat box shape. A large number of specimen-holding containers are mounted on the specimen cassette 75 substantially in the matrix form of 3×3. This specimen cassette 75 is disposed close by the side of the endless conveyor belt 10. Substantially at the same height as its top run 10a. Two parallel transmission belts 76, 77 extending along the reaction line 13 are respectively fixed to the underside of each of both lateral edge portions of the specimen cassette 75. The transmission belts 76, 77 (partly omitted from drawing) are respectively anchored by drive pulleys 78, 79, which are connected to a drive pulse motor 81 by means of a commen shaft 80. The motor 81 moves the specimen cassette 75 to any desired point on the reaction line 13 in parallel therewith. With the foregoing embodiment, the specimen cassette 75 is shown to hold nine matrix arranged specimen containers, whose number, however, is not thus limited. The specimen is formed of, for example, serum obtained from a human body to be examined.

The elongate waste receptacle 47 (FIG. 2A) extends in parallel with the lateral edges of the conveyor belt 10 along the approximately full length of the top run 10a thereof.

A discharge pump assembly 90 shown in FIG. 2A in the block form comprises syringes 93, 94 respectively connected to the first and second reagent nozzles 32 (FIG. 3), 54 through conduits 91, 92 and a syringe 96 connected to the specimen nozzle 71 through a conduit 95. The above-mentioned syringes 93, 94, 96 are respectively connected to the conduits 91, 92, 95 through the corresponding 3-way electromagnetic valves 97, 98, 99.

FIG. 5 indicates an example of a first reagent-pumping assembly used with this invention. One end of the 3-way electromagnetic valve 97 is connected to a deionized water-holding bottle 101 through a conduit 100. A nut member 102 connected to the piston of the syringe 93 is threadedly engaged with a lead screw 103, one end of which is connected to a pulse motor 104.

The pulse motor 104 gives rise to the vertical movement of the syringe 93 through the lead screw 103 and nut member 102. Where the syringe 93 carries out, for example, suction, the deionized water is drawn into the syringe 93 from the deionized water-holding bottle 101 by the changeover of the operation of the electromagnetic valve 97. Later, the discharge action of the syringe 93 causes deionized water to be brought to the tip of the reagent nozzle 32 through a conduit 91. Thereafter, an air bubble is produced at the tip of the reagent nozzle 32 by the slight sucking action of the syringe 93, rendering the reagent nozzle 32 ready to suck up a reagent. Under this condition, the pump system shown in FIG. 5 is only filled with deionized water.

The pump assemblies of the second reagent and specimen have exactly the same construction as that of the first reagent. The syringe-driving section of FIG. 5 including the pulse motor 104, lead screw 103 and nut member 102 can be as designed as to be used in common to the drive of the three syringes 93, 94, 96.

The changeover of the operation of the electromagnetic valves 77, 78, 79 and the drive of the pulse motor are controlled by an output signal from a control circuit.

A nozzle-driving mechanism 105 for effecting the vertical movement of the two reagent nozzles 32, 53 and specimen nozzle 71 is indicated in the block form in FIG. 2A. No detailed description is given of the nozzle-driving mechanism 105 whose construction is already known. This nozzle-driving mechanism 105 comprises a pulse motor 106, rotary disc 107 and drive link 108, one end of which is fixed in the proximity of the periphery of the rotary disc 107. Though FIG. 2A shows only one nozzle-actuating mechanism 105, yet three mechanisms are actually provided to drive the three nozzles 32, 71, 54. The drive link 108 is connected to the conduits 40, 72, 55 of said three nozzles 32, 71, 54. A motor-drive signal is supplied from the later described control circuit 121 to the pulse motor 106.

A spectroscoping section 110 indicated in the block form in FIG. 2A comprises a flow cell 122 for holding a reacted specimen, light source 113 and sensing device 114. Those light source 113 and sensing device 114 are set on both sides of the flow cell 112. A suction nozzle 115 is connected to one end of a conduit 116, the other end of which is connected to the flow cell 112 to supply a specimen thereto. A specimen whose chemical analysis has been brought to an end is conducted to a drain 117. At the spectroscopic section 110, the light absorption of a specimen is determined. Data showing the result of said determination is sent forth to the outside through a signal line 118.

Figure 1:
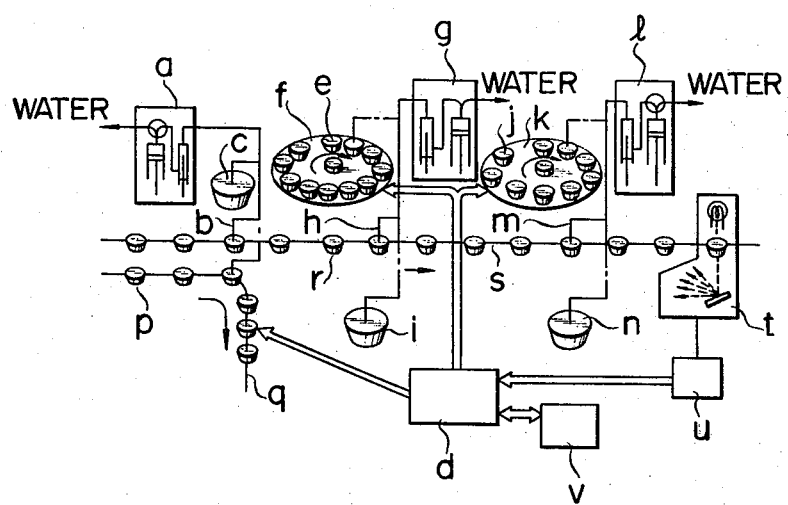
Figure 2B:
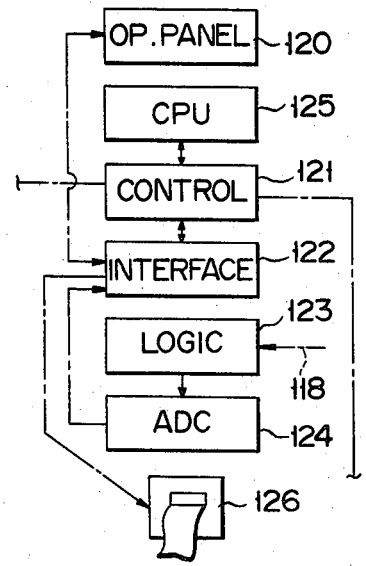
FIG. 2B shows a group of control blocks for controlling the operation of the analytic apparatus of FIG. 2A.

Control blocks 120 to 126 shown in FIG. 2B collectively comprise an operation panel 120 including a keyboard provided with various keys, control circuit 121 for issuing various control signals, interface device for effecting an interface between said control circuit 121 and operation panel 120, log converter 123 for converting a specimen data signal received from the spectroscopic section 110 through the signal line 118 into a signal to be further processed, A-D converter 124 for converting an output signal from the log converter 123 into a digital signal, central processing unit (abbreviated as CPU) 125 for storing a large number of programs corresponding to various items of examination and driving the control circuit 121 and printer 126 for printing out data on a specimen.

The control circuit 121 issues instructions for selectively moving the three movable units 17, 18, 19 along the reaction line 13 to a prescribed extent to the pulse motors 28, 93, 75 through the corresponding signal lines 127, 128, 129. The control circuit 121 further sends forth an instruction for moving the specimen cassette 75 along the reaction line to a prescribed extent to the drive pulse motor 81 through a signal line 130, and also an instruction for the energization of three 3-way electromagnetic valves 97, 98, 99 through the corresponding signal lines 131, 132, 133. The control circuit 121 further produces a drive signal for controlling the operation of the drive pulse motors of the pump assembly 90 through signal lines 134, 135, 136. The control circuit 121 also supplies the nozzle-driving mechanism 105 with a drive signal through signal lines 137, 138, 139. A drive signal is supplied to the drive pulse motors 45, 70, 59 through signal lines 140, 141, 142 to selectively move the two reagent carrier members 31, 53 and specimen carrier member 66 crosswise of the reaction line 13 to a prescribed extent, the above-mentioned drive signals are successively issued from the control circuit 121 in accordance with the programs stored in CPU 125.

Description is now given of the process by which a speimen is chemically analyzed by a discrete type automated chemical analytic apparatus embodying this invention.

The subject chemical analytic apparatus comprising 5 reaction lines or channels as seen from FIG. 2A enables five items of examination to be chemically analyzed at the same time, thereby making it possible to provide more various kinds of first and second reagents. For convenience, however, description is given of the procedure for pipetting a specimen and reagents into the reaction tubes 12 linearly arranged on the central reaction line 13 indicated by a chain line B—B in FIG. 2A.

Reference is made to the chemical analysis of glutamic oxalacetic transaminase (abbreviated as "GOT") in the apparatus of this invention. A program for the chemical analysis of GOT is stored in CPU 125. Various prescribed signals are sent forth from the control circuit 121 when the operator selectively actuates the keyboard mounted on the operation panel 120.

At the start, the carrier members 31, 66, 53 take a position facing the waste receptacle 47, that is, the initial position. The control circuit 121 issues prescribed signals to the respective mechanisms through various lines. The three movable units 17, 18, 19 are moved lengthwise of the reaction line 13 to a pipetting point corresponding to a reaction time desired for the chemical analysis of GOT. For instance, the central movable unit 18 for the pipetting of a specimen is set approximately at a midpoint on the reaction line 13. The movable units 17, 19 for the pipetting of first and second reagents are set almost equidistantly apart from both sides of the central movable unit 18. At this time, the specimen cassette 75 is made to face the central movable unit 18 for the pipetting of a specimen. Specimen-holding containers arranged in a row on the specimen cassette 75 are aligned to a position allowing for suction by the specimen nozzle 71. During this period, the carrier members 31, 66, 53 still retain an original position facing the waste receptacle 47.

After the movable units 17, 18, 19 are moved lengthwise of the reaction line 13 to a prescribed point, two carrier members 31, 53 are guided along the corresponding guide bars 30, 52 from the respective original positions to the desired first and second reagent containers 48, 60. The specimen nozzle-driving carrier member 66 is also guided along the corresponding guide bar 65 to face the desired one of the specimen containers mounted on the specimen cassette 75. The three nozzles 32, 71, 54 are brought down by the nozzle-driving mechanism 105. At this time, the first and second reagents and specimen are sucked up only into the tip portions of the nozzles. Thereafter, the nozzle 32, 71, 54 are pulled up. The carrier members 31, 66, 53 are moved crosswise of the analytic device to the central reaction line 13, causing the first and second reagents and specimen to be pipetted through the nozzles 32, 71, 54 of the carrier members 31, 66, 53 into the corresponding reaction tubes. After the pipetting, the carrier members 31, 66, 53 regain the original positions facing the waste receptacle 47 all at once, thereby causing the solutions left in the nozzles 32, 71, 54 to be drawn off into the waste receptacle 47.

During the above-mentioned pipetting procedure through the nozzles 32, 71, 54 the intermittent drive of the conveyor belt 10 is temporarily stopped. After the above-mentioned pipetting cycle, the conveyor belt 10 is again temporarily moved through a prescribed distance.

The foregoing description refers to the case where the movement of the three carrier members 31, 66, 53 crosswise of the reaction line 13, the drive of the movable units 17, 18, 19 lengthwise of the reaction line 13 and the vertical movement of the nozzles 32, 71, 54 were carried out almost simultaneously. However, the above-mentioned movement may be undertaken independently.

The above-mentioned operation cycle is repeated, each time a specimen is pipetted from the selected one of the specimen containers mounted on the specimen cassette 75. During this period, the specimen cassette 75 is temporarily moved to a point at which a sucked specimen is to be pipetted.

The movable unit 17 for the pipetting of the first reagent takes such a position relative to the central movable unit 18 for the pipetting of the specimen that said movable unit 17 is set on the starting side of the top run 10a of the conveyor belt 10. The above-mentioned position of the movable unit 17 offers the advantage of causing the first reagent to be preheated in the thermostat 14, before a specimen is pipetted into a reaction tube after the first reagent is dripped into said reaction tube. Therefore, this embodiment is adapted for the application of a reagent which has to be particularly preheated. The aforesaid linear arrangement of the movable units 17, 18, 19 along the reaction line in the order mentioned is not limited to that which is adopted in said embodiment.

When a specimen which has been reacted on the reaction line 13 is carried by the conveyor belt 10 to a suction point, that is, a point facing the suction nozzle 115, then said suction nozzle 115 is brought down by the suction mechanism into the prescribed reaction tube to suck up the reacted specimen therefrom. The sucked reacted specimen is conducted to the flow cell 112 through the conduit 116, and then to CPU 125 through the A-D converter 124. The reacted specimen is chemically analyzed in CPU 125. Data on the result of the chemical analysis is printed out by the printer 126 through the interface device 122.

Where an item of examination, namely, the kind of reagent to be applied is changed, then it is advised to provide such a fresh program as causes the first and second reagent nozzles 32, 54 to suck different reagents from other reagent containers 46, 60 mounted on the corresponding base frame members 21, 51.

For convenience of drawing, FIG. 2A indicates the spectroscopic section 110, conduit 116 connected thereto, and suction nozzle 115 only related to the central reaction line 13. Actually, however, this assembly is provided for each of the five reaction lines or channels, thereby enabling data on the result of the examination of five items to be sent forth at the same time.

Where a different specimen is sucked from another specimen container mounted on the specimen cassette, then it is advised to move the specimen cassette 75 lengthwise of the reaction line 13 to a proper extent to cause a row including a specimen container holding a desired specimen to be crosswise aligned with the specimen nozzle 71, and move the carrier member, thereby setting the specimen nozzle 71 at a point facing the desired specimen container.

As described above, a specimen is sucked automatically and quickly from all the specimen containers mounted on the specimen cassette 75 in accordance with a program stored in CPU 125. Two movable units 17, 19 for the pipetting of first and second reagents and the movable unit 18 for the pipetting of a specimen can be moved along the reaction line 13 to a prescribed extent. Further, a specimen and first and second reagents can be quickly pipetted into the reaction tubes mounted on many reaction lines or channels by moving the carrier members 31, 66, 53 crosswise of the reaction lines to a prescribed extent.

A discrete type automated chemical analytic apparatus embodying this invention enables the reagent nozzles and sample nozzle to be moved lengthwise as well as crosswise of the reaction line to a prescribed extent, making it possible to select a proper reaction time and reduce a time of chemical analysis. Particularly where many reaction lines or channels are provided, the subject chemical analytic apparatus has a very useful arrangement, and moreover can be simplified in arrangement. Since the reagent containers and specimen cassette are set close by the side of the reaction line, instead of being positioned on the extension of the reaction line, the distance through which the nozzles are reciprocated for the pipetting of a specimen and reagents can be shortened, thus accelerating the chemical analysis by that extent.

Obviously, the present invention is also applicable to the so-called single channel type chemical analytic apparatus.

What is claimed is:

1. A discrete type automated chemical analytic apparatus for continuously analyzing a large number of specimens with respect to a plurality of items of examination comprising:

conveyor means;

drive means for moving the conveyor mean in a longitudinal direction;

at least one row of a plurality of reaction tubes mounted on the conveyor means in its direction of movement and defining a reaction line, the direction in which the reaction line travels being a time axis direction;

specimen-holding means;

reaction-holding means;

specimen discharge means for pipetting a specimen from the specimen-holding means into a selected one of the reaction tubes arranged on the reaction line, said specimen discharge means including specimen nozzle means;

reagent-discharge means for pipetting a reagent from the reagent-holding means into the selected one of the reaction tubes arranged on the reaction line, said reaction discharge means including reagent nozzle means;

specimen nozzle-driving means for moving the specimen nozzle means from a point at which the specimen nozzle means faces the specimen-holding means to a point facing the selected one of a reaction tubes on the reaction line;

reagent nozzle-driving means for moving the reagent nozzle means from a point at which the reagent nozzle means faces the reagent-holding means to a point facing the selected one of the reaction tubes on the reaction line;

measuring means provided at the terminal end of the reaction line for the analysis of said reacted specimen;

means for washing and drying the reaction tubes in order to render them ready for a subsequent application;

specimen nozzle carrier means for supporting the specimen nozzle means for vertical movement;

said specimen nozzle driving means including first means for moving the specimen nozzle means to a selected point lengthwise of the reaction line in the time axis direction and second means supported by the first means to move the specimen nozzle means to a selected point crosswise of the reaction line whereby to position said specimen nozzle means at a point facing the selected reaction tube;

reagent nozzle carrier means for supporting the reagent nozzle means for vertical movement;

said reagent nozzle-driving means including first means for moving the reagent nozzle means to a selected point lengthwise of the reaction line in the time axis direction, and second means supported by the first means to move the reagent nozzle means to a selected point crosswise of the reaction line whereby to position said reagent nozzle means at a point facing the selected reaction tube;

said reagent-holding means and said specimen-holding means being supported by the first means of the reagent nozzle-driving means and the specimen nozzle-driving means, respectively, to be moved lengthwise of the reaction line in the time axis direction.

2. The chemical analytic apparatus according to claim 1, which further comprises specimen-moving means for driving the specimen holding means to a selected point lengthwise of the reaction line independently of the specimen nozzle means driven by the specimen nozzle-moving means.

3. The chemical analytic apparatus according to claim 2, wherein the specimen-holding means is formed of a rectangular specimen cassette for supporting various specimens in a state arranged in the matrix form; and the specimen-moving means is fixed to the specimen cassette and includes a pair of driving belts extending in parallel along the reaction line.

4. The chemical analytic apparatus according to claim 1, wherein the first means of the specimen nozzle-driving means includes a frame unit set crosswise of the reaction line to traverse the conveyor means, guide bar means extending in parallel with the reaction line to support the frame unit by rolling engagement therewith, belt means fixed to the frame unit in a state extending in parallel with the reaction line, and pulse motor means for driving the belt means;

the second means of the specimen nozzle-driving means includes crosswise set guide bar means fixed to the frame unit in a state set crosswise of the reaction line to traverse the conveyor means and arranged to guide the specimen nozzle carrier means in a slidable state, crosswise extending belt means fixed to the specimen nozzle carrier means in a state stretched across the reaction line, a pair of pulley means supported by the frame unit to anchor both ends of the belt means, and pulse motor means supported by the frame unit in connection to one of the paired pulley means.

5. The chemical analytic apparatus according to claim 1, wherein the first means includes frame unit disposed crosswise of the reaction line to traverse the conveyor means, guide bar means extending in parallel with the reaction line to support the frame units by rolling engagement therewith, belt means fixed to the frame unit in a state extending in parallel with the reaction line, and pulse motor means for driving the belt means;

the second means of the reagent nozzle-driving means includes guide bar means fixed to the frame unit in a state disposed crosswise of the reaction line to traverse the conveyor means and arranged to guide the reagent nozzle carrier means in a slidable state, belt means fixed to the reagent nozzle carrier means in a state stretched across the reaction line, a pair of pulley means supported by the frame unit to anchor both ends of the belt means, and pulse motor means supported by the frame unit in connection to one of the paired pulleys.

6. The chemical analytic apparatus according to claim 4 or 5, wherein the frame unit includes a base frame horizontally traversing the conveyor means and a support arm vertically extending in connection to the respective ends of the base frame; the respective end portions of the crosswise disposed guide bar means are fixed to the corresponding support arms.

7. The chemical analytic apparatus according to claim 6, wherein the conveyor means is formed of an endless belt including a top run and bottom run; the base frame extends through a space defined between the top and bottom runs of the endless belt; and the guide bar means extends in parallel with the base frame over the top run of the conveyor means.

8. The chemical analytic apparatus according to claim 5, wherein at least one reagent container is supported on the frame unit.

* * * * *